United States Patent [19]

Takagi

[11] 3,955,557

[45] May 11, 1976

[54] BLOOD PUMP FOR USE IN AN ARTIFICIAL HEART OR SUCH PURPOSE

[76] Inventor: Hiroyuki Takagi, No. 39-3, Nagane, Narumi-cho, Midori, Nagoya, Aichi, Japan

[22] Filed: Sept. 30, 1974

[21] Appl. No.: 511,024

[30] Foreign Application Priority Data

Oct. 1, 1973  Japan.............................. 48-110329

[52] U.S. Cl..................................... 128/1 D; 3/1.7; 128/DIG. 3; 417/244; 417/389; 417/394
[51] Int. Cl.² ...................... A61M 1/03; A61F 1/24
[58] Field of Search ............ 3/1.7; 128/1 D, DIG. 3, 128/214 R; 417/244, 389, 394

[56] References Cited
UNITED STATES PATENTS

| | | | |
|---|---|---|---|
| 3,020,846 | 2/1962 | Thomas | 128/DIG. 3 |
| 3,182,335 | 5/1965 | Bolie | 3/1.7 |
| 3,881,483 | 5/1975 | Sausse | 128/214 R |

FOREIGN PATENTS OR APPLICATIONS

| | | | |
|---|---|---|---|
| 1,046,098 | 10/1966 | United Kingdom | 128/214 R |

OTHER PUBLICATIONS

"Results of Total Artificial Heart Implantation in Calves", by C. S. Kwan-Gett et al., The Journal of Thoracic and Cardiovascular Surgery, Vol. 62, No. 6, Dec. 1971, pp. 880–889.

*Primary Examiner*—Ronald L. Frinks
*Attorney, Agent, or Firm*—Mason, Fenwick & Lawrence

[57] ABSTRACT

This invention relates to a blood pump for use in an artificial heart including an inlet pump system and an output pump system in series with each pump including branch tubes communicating with first main inlet tube, each branch tube being equipped with a flow-in side valve and a flow-out side valve with a flexible middle portion of the branch tubes which is expanded or contracted to provide a pulsatile pump with flow-out end of each branch tube connected to a second main tube with the second main tube of the inlet pump system being connected with the first main tube of the output pump and with the branch tubes of each system being ultimately expanded and contracted at different rates to provide a blood pump which achieves excellent hemodynamic effects without requiring synchronization with the rhythm of a natural heart.

4 Claims, 3 Drawing Figures

BLOOD PUMP FOR USE IN AN ARTIFICIAL HEART OR SUCH PURPOSE

This invention relates to a pump for use in an artificial heart.

It is required physiologically that the pump for the artificial heart should be pulsatile. Since the flow which is pumped out of the pulsatile pump is not continuous but intermittent, the flow into such a device is also intermittent. Therefore, any type of pulsatile pump, such as sack-type, diaphragm-type, or piston-type, can accept the blood into the device only during the expansion period of pumping cycle.

Generally speaking, any pump system needs a reservoir to create a smooth flow. Such a reservoir, however, is not provided in the circulation system of a human body. Reservoirs in artificial hearts are undesirable because the stagnation of the blood flow in the reservoir increases the incidence of thrombus formation. Therefore, the pump system of an artificial heart has to have particular characteristics as follows:

i. Pressure and flow wave curve created by pumping in the flowout tube should be as similar as possible to that created by a natural heart, ii. Device has to get blood as much as possible during only an expansion period of a pumping cycle, iii. Inflow into the device should be as smooth as possible without any reservoir under the condition of low pressure gradient between circulation system of the body and the device.

Unfortunately, prior artificial hearts or left heart assisting devices have not achieved these characteristics of output, and no effort has been made to the characteristics of inflow.

One pumping cycle of a pulsatile pump consists of two phases, one is compression and another is expansion phase. On the pumping of the artificial heart, the compression phase requires a time interval such as 300 msec. because the device pumps out blood against the aortic pressure similar to the action of the natural heart. When pumping at 100 times per minute, only 300 msec. are available for expansion during which the device must provide sufficient blood under the condition of low pressure gradient without a reservoir. Since left atrial pressure is less than 10 mmHg., it is necessary to produce a high negative pressure in the pump system to quickly suck blood into the device. Sometimes, however, a part of the left atrial wall may be sucked in the orifice of the flow-in tube, which may cause a fatal thrombus formation.

The present invention is concerned with a pump for use in an artificial heart, which has solved the problems described above.

The invention is explained in greater detail by way of an embodiment illustrated in the accompanying drawings, in which.

Figure 1:
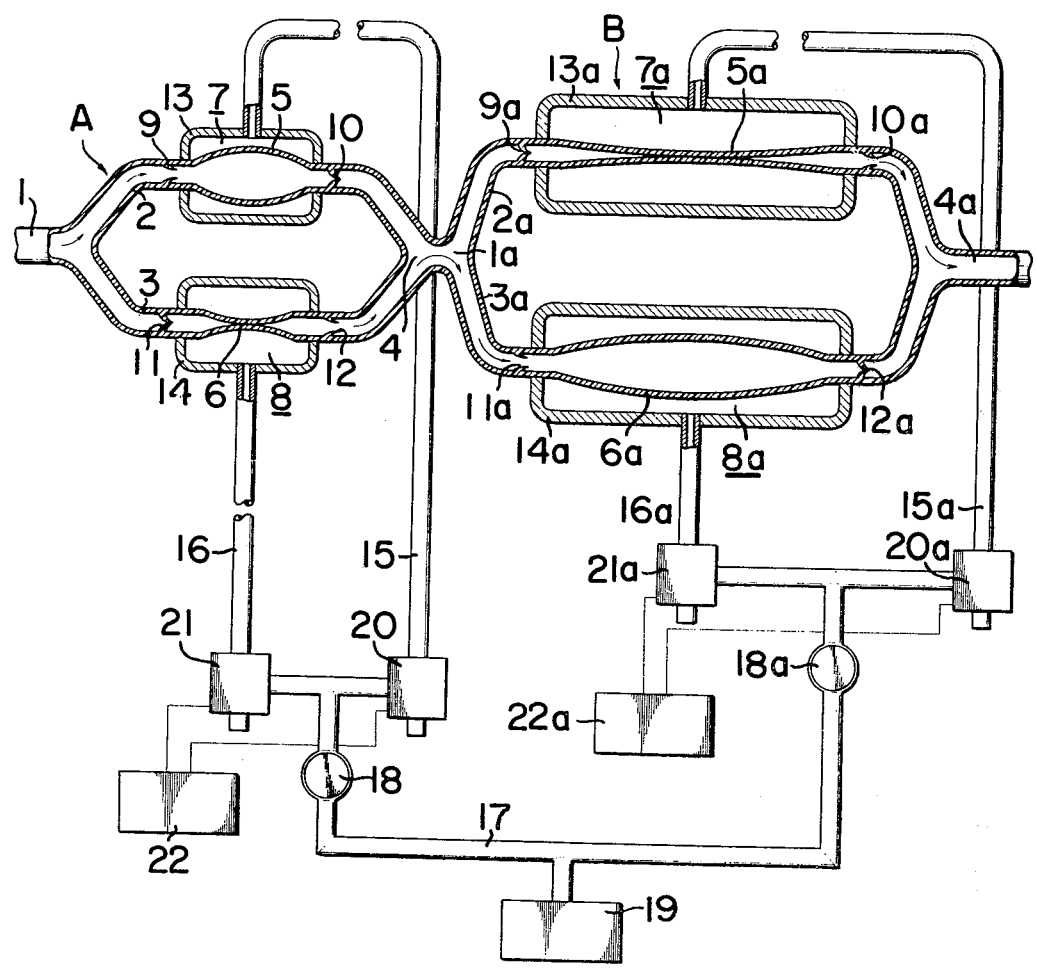
FIG. 1 is a partially cutaway front view of a pump according to the invention.
Figure 2:
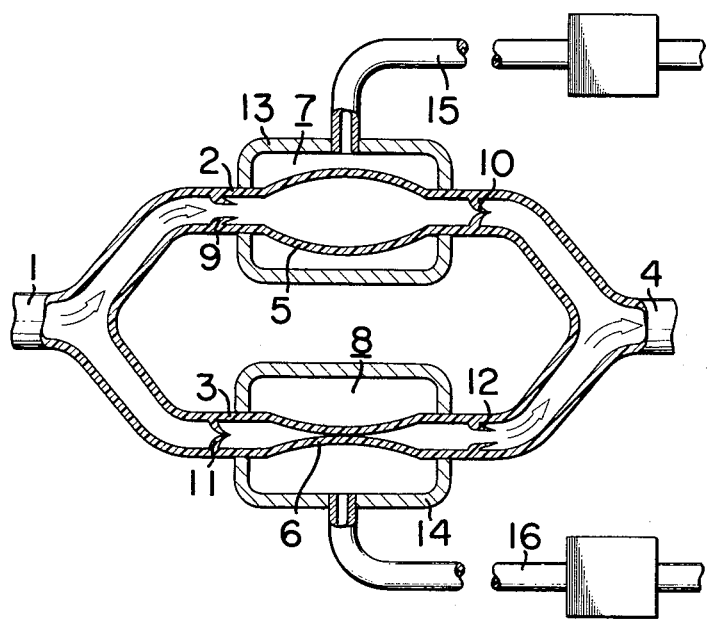
FIG. 2 is a partially cutaway front view of the essential portion of the pump shown in FIG. 1.
Figure 3:
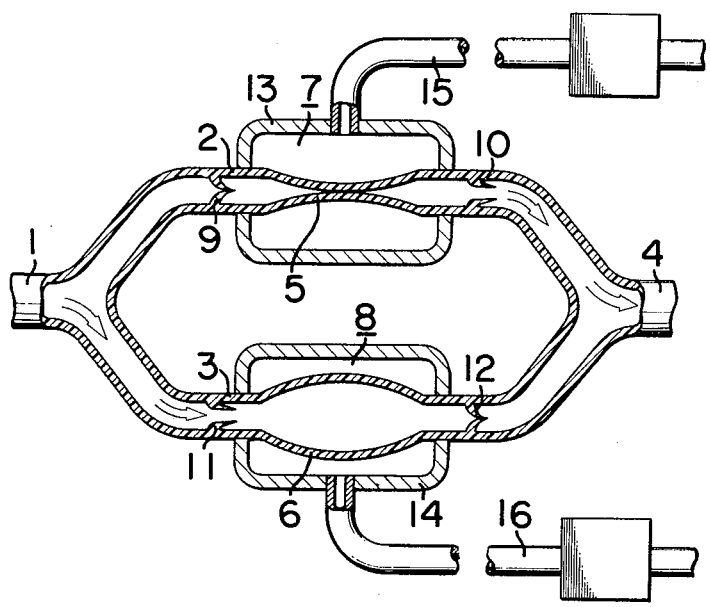
FIG. 3 is the partially cutaway front view of the essential portion shown in FIG. 2 with the expansion and contraction of the opposite branch tubes reversed.

Reference numeral 1 is a tube at the flow-in side, which is fabricated of antithrombogenic material, such as silicone rubber. This tube 1 is separated into two branch tubes 2 and 3, made of same material and integrated with another tube 4, made of same material.

At the middle portion of tubes 2 and 3 each of tubes 2, 3 is bulged out to form chambers 5, 6 of sack-type pulsatile pumps respectively 7, 8.

At the flow-in and flow-out sides of each pulsatile pump 7, 8, valves 9, 10 and 11, 12, are provided respectively. Shells (housings) 13, 14 are provided around the each chamber 5, 6 and on each shell, air tubes, 15, 16 through which compressed air is supplied to the pumps 7, 8 are provided. On each line of air-tubes 15, 16, which are connected via a duct 17 with a pressure regulator 18 and compressor 19 at the end, three-way solenoid valves 20, 21 are interposed respectively.

These three-way solenoid valves are driven by controller 22, which controls the pumping cycle of each pump to be alternate, not simultaneous, as follows;

Pumping mode:

When one pump is in the compression phase of the pumping cycle, the other is in the expansion phase. When one is switched to the expansion phase from the compression phase, the other is simultaneously switched to the compression phase from the expansion phase. Thus, pumping of each pump is alternate, not simultaneous. Therefore, flow into the device is not intermittent but steady because one of two pumps is always in the expansion phase while the outflow of the device is completely pulsatile.

Compression-expansion ratio:

Originally, compression expansion ratio of each pumping cycle is 1:1. Since negative pressure is not desired on this system as described before, actual compression is quickly achieved with highly compressed air and actual expansion is achieved slowly with no suction. There should be a time delay to some extent. Therefore, shorter compression and longer expansion are much better to obtain a smoother flow into the device. In such a case, compression of one pump is terminated shortly before the other pump begins compression. This time would be determined according to the pumping rate when compression-expansion ratio is 1:1. Therefore when one pump is switched from the compression phase to the expansion phase, the other pump is still the expansion phase. The expansion phase of the other pump is terminated at the original time which is determined when compression-expansion ratio is 1:1, and switched to the compression phase. In such a case, alternate pumping is not exactly correct but actually occurs as follows:

i. Alternate compression period, which is slightly shorter than original one;

ii. Then simultaneous expansion period, which is a very short time interval, such as 50 msec. or 75 msec., etc.;

iii. Then original alternate expansion period.

Whenever pulsatile rate created by pumping must be low according to the body's demand, an extra pump system (B) is added at the end of flow-out tube 4.

At the end of the tube 4, the flow-in tube 1a is connected.

The tube 1a is separated into two branch tubes 2a, 3a, which are integrated with another tube 4a at the flow-out side. The middle portions of branch tubes 2a, 3a are bulged out respectively as chambers 5a, 6a of sack-type pumps 7a, 8a the same as the chambers 5, 6 of system (A). Valves 9a, 10a and 11a, 12a are provided at both the sides of each of the chambers 5a, 6a.

Housings (shells) 13a, 13b, air-tubes 15a, 16a, three way solenoid valves 20a, 21a are provided on each of the pumps 7a, 8a, to each of which compressed air is supplied from the compressor 19 through pressure regulator 18a.

When pump systems (A) and (B) are connected with each other in series like this, (A) and (B) are driven by each of controllers 22, 22a independently. In such a case, the pumping mode of (A) is adjusted to get smoother intake while pumping mode of (B) is mainly adjusted to have better characteristic of output according to the body's demand.

However, when both the systems are relatively similar to each other, one of them can be omitted.

The pump system A or A+B constructed by the present invention has an advantage in that either of two pulsatile pumps 7, 8 arranged in parallel is always receiving blood as a steady flow, while they create pulsatile flow in flow-out tube. Therefore, it is possible to eliminate the various drawbacks occurring in conventional single pulsatile pumps as follows:

i. Quick intake of blood into the device only during the expansion period requires the development of negative pressure on the system in order to increase the pressure gradient between the body and the device. Negative pressure, however, draws part of the left atrial wall into the tube at times because there is no reservoir in the body and in the pump system. Such a complication is markedly decreased by the present invention.

ii. Increased efficiency of inflow makes it possible to reduce the cross-sectional area of the tube. Smaller tubes make a surgical operation with the artificial heart easier and decreases the complications which may occur.

iii. In addition, the blood flows without stagnation as a steady flow. This device significantly decreases the incidence of thrombus formation.

iv. Furthermore, the pump for an artificial heart according to the present invention has another important advantage which is of most value in clinical use.

When the present pump is connected with the left ventricle, the whole blood in the left ventricle is continuously sucked out into the device. The left ventricle cannot, therefore, generate any pressure because it contains insufficient blood.

Since the left ventricle does not generate any pressure, as shown in the following examples, pumping of the artificial heart does not require synchronization with the rhythm of the natural heart. The controller can, therefore, be simplified.

EXAMPLE 1

Pump system (A) which consists of two sack-type pulsatile pumps in parallel, as described before, was connected to a dog as a bypass-type left heart assisting device, in that, the flow-in tube was connected with the apex of the left ventricle and the flow-out tube was connected with the aorta. Each chamber of this pump has a capacity of 15 ml.

In this example, pumping condition was as follows:
expansion: compression=1:1, alternate pumping.

Pumping rate per minute was 120 on each chamber. Inflow was steady and outflow was pulsatile with the pulse rate at $120 \times 2 = 240$ which, of course, was not in synchronization with the natural heart.

During pumping, the aortic flow was 0. This fact shows there was no output through the aortic valve to the aorta through the natural heart, with the bypass-pump maintaining the systematic circulation. The left ventricular pressure was 0 mmHg. In this example, the pumping rate was too high and the pulse wave in the aorta was too much.

EXAMPLE 2

When pumping rate is reduced to 90 on each chamber of the pump system (A) of the same type, the pulse wave in the aorta decreased to $90 \times 2 = 180$, though it is still higher than normal. During pumping, however, the left ventricular pressure decreased to 0 mmHg, while the aortic pressure increased to 120 mmHg. In this example, the decrease of left ventricular work load is maximum, while the systematic circulation is maintained at a normal level.

Since this pump system does not need synchronization with the rhythm of the natural heart, excellent hemodynamic effects are achieved which have never been obtained by the pumping of any type of left heart assisting device in the world.

EXAMPLE 3

An extra pump system (B) with each chamber having a 20 ml capacity, was connected in series to the pump system (A).

The pumping rate of pump system (A) was $90 \times 2 = 180$ and the pumping rate of pump system (B) was $55 \times 2 = 110$. Therefore, the aortic pressure wave is almost similar to that during non-pumping condition.

Low aortic and left ventricular pressures produced by the ligation of the left coronary artery were suddenly improved by the pumping of these pump system (A + B) so that the aortic pressure increased to normal and systematic circulation was maintained at the normal level.

Left ventricular pressure decreased to less than 0 mmHg which was the same as in Example 2.

What is claimed is:

1. A blood pump for use in an artificial heart or the like, said pump comprising an intake main tube, an output main tube, a connecting tube, an intake pump system and an output pump system connected in series with each system including two flexible branch tubes, a flow-in side leaflet valve and a flow-out side leaflet valve in each branch tube, said branch tubes in the intake pump system communicating at their in-flow ends with the intake tube and communicating at their flow-out end with a first end of the connecting tube, said branch tubes in the output system communicating at their in-flow end with the connecting tube and communicating at their flow out end with the output tube, means for alternately collapsing and expanding the branch tubes in each system with the frequency of pulsation of the intake pump system different from the frequency of the output pump system thereby providing a blood pump which does not require synchronization with the rhythm of the natural heart.

2. The blood pump of claim 1 wherein the means for alternately collapsing and expanding the branch tubes in each system includes enclosures surrounding a portion of each branch tube between the flow-in valve and the flow-out valve of that tube and means for charging compressed air into each enclosure and discharging the compressed air from each enclosure in timed sequence.

3. The blood pump of claim 2 wherein the charging and discharging means includes an air compressor, air tubes operatively connecting the compressor with each of the enclosures, valve means on each of the air tubes for selectively isolating or communicating each enclosure to the compressor, venting means for selectively isolating or communicating each enclosure to the atmosphere and a control means for alternately opening the valve means and the vent means on each enclosure.

4. The blood pump pf claim 3 wherein the valve means and vent means are a three-way solenoid valve on each of the air tubes.

* * * * *